United States Patent [19]

Cook et al.

[11] Patent Number: 5,250,235
[45] Date of Patent: Oct. 5, 1993

[54] METHOD OF MAKING LASER-WELDED INTRAOCULAR LENSES

[75] Inventors: James R. Cook, Boca Raton, Fla.; Clarence L. Shuff, Huntington, W. Va.

[73] Assignee: Chiron Intraoptics, Inc., Irvine, Calif.

[21] Appl. No.: 872,614

[22] Filed: Apr. 22, 1992

[51] Int. Cl.$^5$ .............................................. B29D 11/00
[52] U.S. Cl. ........................ 264/1.4; 219/121.61; 219/121.64; 264/1.7; 264/25; 264/40.1; 156/272.8
[58] Field of Search ............... 264/1.4, 1.7, 22, 25, 264/40.1; 219/121.61, 121.63, 121.8, 121.64; 623/6; 156/272.8

[56] References Cited

U.S. PATENT DOCUMENTS

| | | |
|---|---|---|
| 3,994,027 | 11/1976 | Jensen et al. |
| 4,104,339 | 8/1978 | Fetz et al. |
| 4,469,098 | 9/1984 | Davi ........................... 219/121.8 |
| 4,786,445 | 11/1988 | Portnoy et al. |
| 4,834,749 | 5/1989 | Orlosky ........................ 264/1.4 |
| 4,843,209 | 6/1989 | Milligan et al. |
| 5,118,452 | 6/1992 | Lindsey et al. .................... 264/1.7 |

FOREIGN PATENT DOCUMENTS 59-174289  10/1984  Japan .............................. 219/121.61

Primary Examiner—Jeffery Thurlow
Assistant Examiner—Mathieu Vargot
Attorney, Agent, or Firm—Pravel, Hewitt, Kimball & Krieger

[57] ABSTRACT

The invention provides laser-staked intraocular lenses and a method for producing these lenses. The invention method uses a apertureless Nd YAG laser for staking PMMA fixation members onto PMMA lens optic bodies. The resultant laser-staked lenses are free of heat-induced optical deformities and mechanical blemishes and have a strong bond at the junction between the optic body and the fixation member without gaps for the potential accumulation of bio-burden.

3 Claims, 1 Drawing Sheet

METHOD OF MAKING LASER-WELDED INTRAOCULAR LENSES

BACKGROUND OF THE INVENTION

1. Field of the Invention

This invention relates to intraocular lenses and methods of affixing fixation members to intraocular lenses. More specifically, this invention relates to the use of a neodymium yttrium aluminum garnet (Nd YAG) laser for the staking of fixation members to the optic bodies of intraocular lenses. These laser-staked lenses are substantially free of heat-induced optical deformities and provide a strong bond at the junction between the optic body and the fixation member without gaps for potential accumulation of bio-burden.

2. Description of the Related Art

It has become a routine practice to implant intraocular lenses after a patient has had cataract surgery to remove the natural human lens. These lenses generally include a plastic lens optical body which is designed to focus light, and a fixation member for holding the lens in place in the eye.

Fixation members vary widely in design and include iris clips of various configurations and haptics of various shapes, including the now-popular "J-shaped" haptics. Haptics now often comprise a pair of opposed outwardly disposed thin loops for holding the lens in place in the posterior chamber of the eye.

Fixation members may be fabricated of a suitable biocompatible material, such as platinum-iridium wire, or plastic loops made of a thermoplastic material, such as polypropylene, or a thermosetting material, such as polymethylmethacrylate.

U.S. Pat. No. 4,104,339 states that extracapsular lenses normally have one pair of opposed outwardly disposed loops, generally of metal wire such as platinum-iridium, and which are designated "posterior loops" because the ends are attached into and through the rear face or base of the lens. The four ends of the two loops are generally arranged in a square pattern at distances of about 1 mm from the center line of the lens, outside the immediate line of vision of the wearer. Loop wires are of 0.15 to 0.20 mm diameter and extend downwardly from the base of the lens.

The '339 patent claims as its invention a method of connecting fixation members of thin metal wire to a thermoplastic intraocular lens body. In this method, loops are positioned in a chuck and are heated by passing electricity through the chuck's clamp jaws to cause inductive heating of the wire material to slightly above the melting point of the plastic material of the lens body. The ends of these heated wire loops are then pushed into the peripheral edge of the lens body. Upon cooling, the ends of the wire loops are said to be firmly secured to the lens body. When the loops are fabricated of plastic line, holes are first drilled into the side walls of the lens body, less than halfway through the lens body. The ends of the loop are then inserted into these holes in the lens body and are heat-fused at a point along the inserted length to the lens material. This heating is accomplished by pushing a thin probe inductively heated to above the melting point of the lens material through the base of the lens body until it contacts the loop line material. It is represented that only the material in the immediate vicinity of the probe entry point is melted and the resulting heat-deformed ring is said to be about three times the diameter of the probe. Therefore, this method of attachment by use of a heated probe is akin to spot welding so that fusion of the loop line ends and the lens body only takes place in the vicinity of the point of contact with the heated probe. Consequently, it may be expected that the polymeric loop ends would not be as tightly attached to the lens body as when the entire inserted loop end is melted, caused to flow, and thereby bonded and attached to the lens body. Further, it might be expected that there would be gaps between the inserted polymeric loop line ends and the walls of the holes in the lens body. These gaps may be expected to provide a space for microbial contamination or "bio-burden" and prevent ready sterilization of the heat staked intraocular lens.

U.S. Pat. No. 3,994,027 is directed to a pre-pupillary lens of polymethylmethacrylate having a planar and a convex surface and having a pair of posterior loops embedded and fused into the optic portion. In a second embodiment, the lens includes a pair of anterior loops with their ends inserted in a set of two parallel bores which are disposed in a plane between the planar and convex surfaces of the lens. The loops are formed of platinum-iridium wire and are heated to a temperature in the range of 125-200° C. before being embedded into the lens optic. The '027 patent also discloses the use of "an electronic bonder" to apply to a "heat tack" to the surface of a lens, adjacent the borehole into which the loops fit. It is represented that this heat tack fuses the ends of the loop to the lens body.

U.S. Pat. No. 4,786,445 is directed to a method of affixing fixation members to an intraocular lens by using laser energy to cause melting of inserted ends of the fixation member. In this method, a hole is drilled in the periphery of the optical body and a shoulder is formed within the hole near its inner end. One end of a fixation member is fitted into this hole and laser energy in the near infrared band is applied to cause the inserted end of the fixation member to melt and flow behind the shoulder. Upon cooling, the flowable portion of the fixation member hardens within the shoulder of the hole and forms a mechanical interlock which resists rotation and withdrawal of the fixation member from the cavity. In other embodiments the hole is tapped and provided with screw threads so that when the inserted end of the fixation member melts and flows, it flows into the threading. Upon hardening, the mechanical interlock between the threads and the flowed portion of the inserted end of the fixation member resists withdrawal of the fixation member.

U.S. Pat. No. 4,843,209 is directed to an apparatus for laser heat staking of intraocular lenses. The method uses a computer-controlled Nd YAG laser with a helium neon (HeNe) aiming laser which feeds a fiber optic multiplexer controller. As a result, several workstations can be operated at one time. The workstations have x-y work tables fitted with carousel holders into which intraocular lenses are placed for staking. A laser stylus is manipulated into position above the junction of the optic and the fixation member. The laser is then energized, fusing the inserted ends of the fixation member in the hole of the optic. It is represented that, as the haptic is lased, the haptic material within the optic swells. This, in combination with the internal fusion and melting, effectively seals the majority of the haptic hole to produce an intraocular lens with reduced potential of bio-burden. It is suggested that the optic does not melt because the polymethylmethacrylate material is about 95% transparent to YAG laser energy as long as its power density does not exceed the plastic's threshold temperature. It is further represented that a pigmented haptic loop, which will absorb more laser energy, and which fuses or heats faster, can also be used. It is represented that a continuous wave Nd YAG laser beam of 25 watts power applied for 1.5 seconds is sufficient to bond haptic to optic. However, in applying the method as explained in the '209 patent, it has been found in practice that blemishes are formed on the optic surface at the point of laser contact and the fixation members are not firmly attached.

What is yet needed is a method of staking intraocular lenses that is simple, reliable, and relatively inexpensive, that allows the staking of PMMA fixation elements to PMMA optics, that avoids rotation and misalignment of the fixation elements during staking, that reduces gaps between the fixation element and the borehole in the lens optic for reducing the potential for bio-burden accumulation, that attaches the fixation element firmly to the optic, and that does not adversely affect the optical properties of the lens in the vicinity of the staking process.

SUMMARY OF THE INVENTION

The invention provides a laser-staked intraocular lens (IOL) that has a firmly affixed fixation element and that is substantially free of heat-induced blemishes, when viewed under a 10X magnification, in the region of the laser-staking. Further, there are no significant gaps between the outside surface of the fixation element and the inside surface of the borehole of the lens optic for potential accumulation of bio-burden. The invention laser-staking process avoids rotation and misalignment of the fixation element that may occur during heat staking with a hot probe. Further, in the process, the inserted ends of the fixation element flows and blends with the material of the optic body so that the fixation element is strongly bonded to the optic body.

The fixation elements suitable for use in the invention include polymethylmethacrylate (PMMA) lines having a blue innercore covered with a thin sheath or coating of clear PMMA. Prior to staking, small holes are drilled into the optic portion of the IOL for receiving the ends of the fixation elements. The ends of PMMA loops are then inserted into the receiving holes and the assembled intraocular lens is placed on the x-y table of an Nd YAG laser for staking. A CCTV camera and monitor is focused on the area to be staked and the x-y table is then adjusted until the fixation element-optic junction is directly within the cross hairs of the aiming monitor. At this point, the Nd YAG laser is energized for up to about 1.5 seconds at a wave length of about 1064nm, in a diffused beam about 12 the controlling apertures from the laser, thereby staking the haptic firmly to the optic.

While not wishing to be bound by any theory, it is theorized that the diffused Nd YAG laser energy passes through the clear PMMA optic and is absorbed into the blue core of the fixation element. From this blue core, the energy then travels by conductive heat waves outward until it reaches the thin PMMA sheath or coating. Although it may be expected that heat would be more intense in the core of the PMMA fixation element, melting occurs preferentially at the sheath because of its relative thinness. Thus, it is theorized that heating of the core causes the PMMA fixation element to swell while heating of the sheath causes the sheath to melt and flow. This combination of swelling, melting and flowing causes the inserted end of the fixation element to blend with the optic body sealing the receiving hole and providing a strong, permanent bond substantially without heat-induced blemishes or defects, when viewed under 10X magnification, and capable of withstanding a 50 gram pull force applied to the fixation element.

The invention method using a diffused Nd YAG laser energy beam provides a laser-staked blemish-free IOL with firmly attached fixation elements and a simple, relatively inexpensive method of producing this high quality IOL.

DETAILED DESCRIPTION OF THE PREFERRED EMBODIMENTS

The invention provides a method for the laser-staking of fixation members to the optic bodies of intraocular lenses (IOLs). The laser-staking method produces an intraocular lens that is substantially free of heat-induced or mechanical blemishes, when viewed under 10X magnification, in the region where the fixation member attaches to the optic body. This substantially eliminates the "blue light" or prismatic halo effect that intraocular lens recipients sometimes experience as a result of defects at the periphery of the IOLs caused by surface blemishes which result from mechanical or heat-induced methods of affixing the fixation member to the lens optic body.

In the invention method a lens optic is selected and holes for receiving the ends of fixation members are drilled into the periphery of the lens. These holes may be drilled with any conventional drilling machine adapted for use with IOLs. Such machines are commercially available and are generally fitted with adjustable stops so that the user may control the depth to which any hole is drilled. It is preferred that the receiving holes should be cylindrical with smooth sides. Further, these holes need only be drilled to a depth of about 0.025 thousandths of an inch.

Figure 1:
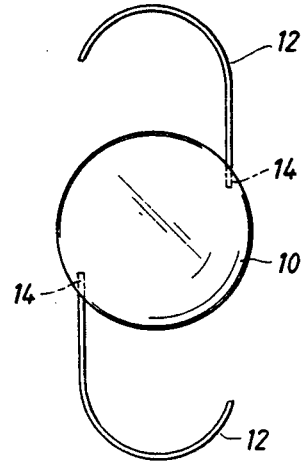
FIG. 1 is an intraocular lens with J-loop or other loop haptics attached.
Figure 2:
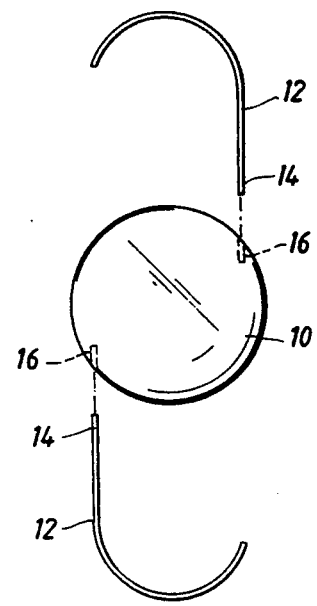
FIG. 2 is an optic body of a lens with holes drilled into the periphery for receiving the ends of fixation members.

FIGS. 1 and 2 show an embodiment of an intraocular lens fitted with J-shaped haptics. The lens includes a body 10 and 2 J-shaped haptics 12. The ends of the haptics 14 are embedded and affixed to the lens 10 as shown in FIG. 1. In order to so affix the haptic ends 14 to the lens body 10, holes 16 are conventionally drilled into the peripheral edges of the optic body 10. While FIGS. 1 and 2 show representative examples of typical intraocular lenses with J-shaped haptic loops, other fixation elements may be used. These include iris clips and fixation members of shapes other than J-shaped haptics.

Fixation members are prepared by bending thin PMMA strands into shape and heat-treating them in water at about 72-75° C. to obtain a fixation member of the desired configuration. These fixations members are then cut and trimmed to size before their ends to be staked are fitted into the receiving holes in the lens optic body. The preferred fixation member material is fabricated from PMMA and comprises a blue dyed core uniformly coated with a thin layer of clear PMMA.

The IOL, with fixation members inserted into the receiving holes, is then placed on a lens holder 50 designed to hold one or several lenses and their fixation members in a fixed position. This lens holder is preferably keyed for accurate repetitive placement on the x-y table 44 of a laser-staking workstation.

The laser apparatus used in the invention method emits a continuous wave Nd YAG laser beam having a wavelength of approximately 1064 nm. The apparatus is preferably modified by the removal of all apertures so that the full beam from the laser producing rod is emitted. The diameter of such a beam is about 12 thousandths of a inch in the case of the Model 9560 CW Nd YAG laser produced by Laser Applications, Inc. of Orlando, Fla. which has an output power of 14 watts. During the lasing action, the energy is applied in a continuous wave form without pulsing.

The x-y table of the laser-staking workstation is then manually positioned so that the junction between the end of the fixation element and the receiving hole of the optic body is centered below the Nd YAG laser stylus. This may be achieved by the CCTV-monitor apparatus or alternatively this may be achieved by using a HeNe laser which provides a red light and which can be centered onto the haptic-optic junction. Desirably an image of this junction is obtained on a CRT screen so that proper centering can be readily ascertained. Further, desirably the monitor HeNe laser is equipped with cross-hairs for accurate aiming. Once the fixation member-optic body junction is targeted, the Nd YAG laser is manually turned on for a period of about 1.5 seconds. This produces energy at 1064 nm in a multi-mode wave diffused beam since the apertures normally used for controlling the diameter of the beam are removed from the laser. This diffuse burst of energy is sufficient to stake the fixation member to the optic.

Figure 3:
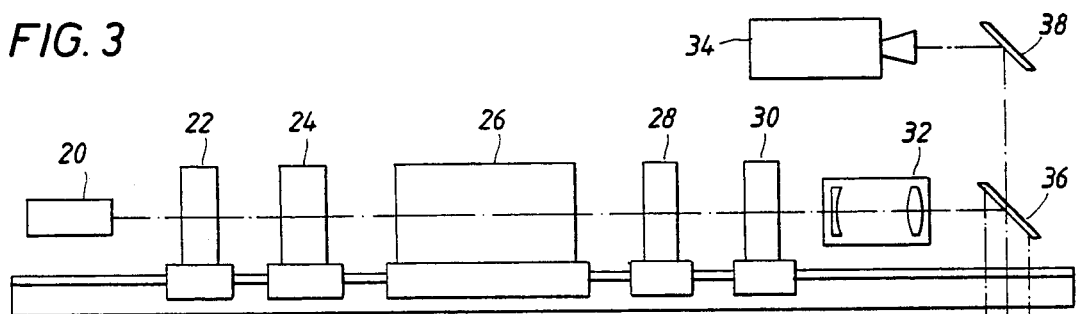
FIG. 3 is a schematic diagram of the laser welding apparatus.

The operation of the laser-staking apparatus may be better understood with reference to a schematic representation of the apparatus shown in FIG. 3. A helium-neon laser 20 is mounted co-axially behind a YAG laser in a chamber 24 so that its visible, red beam will align with and be concentric with the YAG beam to facilitate alignment of the YAG beam onto a workpiece on an x-y table 44. The laser beams pass concentrically through a rear mirror 22 which is used for lensing of the YAG rod to generate laser power. Usually, the beam passes through a Q-switch which prevents lasing action for more than 99% of the laser's duty cycle. Laser output is then typically produced intermittently in the form of short pulses. The invention system does not use Q-switching. Chamber 24 houses the YAG rod and its optical pump source, arc lamps. The laser head 26 contains a chamber designed to efficiently focus the optical energy from the arc lamps to the YAG rod. The beam passes through a shutter 28 which determines the diameter of the beam. In the invention system, the shutter is removed so that the YAG laser beam is diffused. The diffused laser beam passes through front mirror 30 and up collimator 32 before being deflected by dichoric mirror 36 and focusing lenses 40 and 42 onto a point on the workpiece. The position of the focused laser beam point on the workpiece may be varied by moving the x-y table 44. This may be effected by first viewing the workpiece through a closed-circuit television screen which receives its signal from television camera 34 which in turn is aligned with the laser beam by means of deflection mirror 38. Then the image on the closed-circuit TV screen is observed and the x-y table 44 is manipulated into position by turning positioning screws attached to crank handles 46 and 48.

Figure 4:
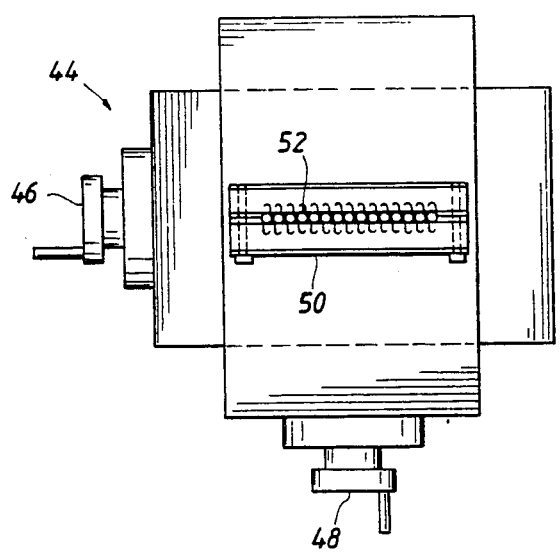
FIG. 4 illustrates a jig or fixture used for holding one or more intraocular lenses with attached haptics on an x-y table for laser-staking.

From FIG. 4, it can be seen that one or several lenses 52 may be placed in a lens holder or jig 50 which is clamped to the base-plate 54 of an x-y table 44. Thus, by suitably manipulating crank handles 46 and 48, a series of laser welds can be carried out on lenses 52. The lens holder or jig 50 is designed to hold the fixation elements in the holes drilled within the lens bodies. For example, a jig would hold ends 14 of J- or other shaped haptics 12 in the holes 16 in lens body 10 so that the parts of FIG. 2 resemble the assembly of FIG. 1. The laser then stakes ends 14 into receiving holes 16.

While not wishing to be bound by any theory, it is believed that during laser-staking, energy from the Nd YAG laser passes through the clear PMMA lens optic and the clear PMMA coating on the fixation member and is absorbed into the blue core of the PMMA fixation member. The energy then flows outward from the core by conduction heat until it reaches the surface of the fixation member which cooperates with the inner surface of the cylindrical hole in the optic body. The heat also causes the end of the fixation member to expand thereby filling any gaps between the surface of the haptic member and the receiving hole. Further, at least a portion of the surface of the PMMA fixation member melts and flows so that, upon removal of the laser energy and cooling of the haptic, the PMMA of the fixation member has commingled with the PMMA of the optic body. Thus, after laser-staking there is no discernable difference or fine line demarcation between the clear coating or sheath over the blue core haptic and the optic body. Indeed, only the blue core remains as visible evidence that the end of a fixation member was inserted into the optic body. The surface of the IOL produced is free of heat-induced or mechanical damage. It is further theorized that the usual concentrated burst of energy produced when a aperture is used to restrict the diameter of the laser beam to about 6 thousandth of an inch is too hot and therefore does not produce the desired staking. However, the use of a apertureless laser with a diffuse 12 thousandths of an inch diameter beam produces energy at the level necessary for staking and provides a strong attachment of haptic to optic.

In order to test the strength of the bond between the optic body and the fixation member, the laser-staking IOL is clamped to a fixture with the fixation members pointing outward. A 50 gram weight is hooked onto the fixation member. The invention laser-staked lenses withstand this 50 gram pull test with fixation member firmly in place.

It should be emphasized that the use of polypropylene or other thermoplastic haptics is not preferred. Rather, a low melting point thermosetting material that swells slightly upon being heated is preferred. Of those materials PMMA is FDA approved for use in IOLs and is the preferred material.

Tests were carried out to determine whether laser staking might produce any adverse biological or chemical effects.

EXAMPLE 1

A monolayer of L-929 mouse fibroblast cells was grown to confluency and overlaid with Minimum Essential Medium supplemented with serum, antibiotics, neutral red, and agarose. A laser staked lens test sample was placed on the solidified overlay surface. Following incubation for 24 hours, the culture was macroscopically examined for evidence of cell decolorization to determine the zone of cell lysis. Any decolorized zone present was examined microscopically to confirm cell lysis.

| Score | Observations |
|---|---|
| N (Nontoxic) | No change in cell morphology in proximity to test sample. |
| T (Toxic) | Death and/or degeneration of cells directly beneath the area of test sample and possibly also within a zone extended beyond the test sample. Where a zone of lysis was observed, the distance from the edge of the sample to the edge of the zone was measured and reported in millimeters (mm). |

The results of the tests were as follows:

| Test/Control Articles | Score | Zone of Lysis (mm) |
|---|---|---|
| Test Article Results | N | 0 |
| Negative Control (USP Plastic) | N | 0 |
| Positive Control: P-11102 | T | 10 |

From these results, it is concluded that the laser staked lens was nontoxic for L-929 mouse fibroblast cells.

EXAMPLE 2

Samples of PMMA haptics, laser-staked lenses and non-laser staked lenses were analyzed by gas chromatography to determine the proportion of methylmethacrylate monomer (MMA) content. The results were as follows:

| Sample | % MMA |
|---|---|
| PMMA Haptics | 0.18 |
| Laser Staked Lenses | 0.55 |
| Non-Laser Staked Lenses | 0.61 |

The monomer content of the laser and non-laser staked lenses does not appear to be significantly different.

Although the invention has been described in terms of specific embodiments which are set forth in detail, it should be understood that this is by way of illustration only and that the invention is not limited to the specific embodiments. Alternative embodiments and operating techniques will become apparent to those skilled in the art in view of the disclosure. Accordingly, modifications which can be made without departing from the spirit of the invention as described above are within the scope of the invention and claimed herebelow.

What is claimed is:

1. A method of affixing fixation members to the optical portion of an intraocular lens, comprising:

selecting a polymethylmethacrylate intraocular lens optic with at least one receiving hole having a cylindrical inner surface in the periphery of the lens optic for receiving one end of a fixation member having a cylindrical outer surface;

inserting one cylindrical end of a fixation member, having a blue core surrounded by a thin sheath of polymethylmethacrylate, into the receiving hole in the periphery of the lens optic;

positioning the intraocular lens optic with inserted fixation member on the x-y table of an Nd YAG laser from which the beam-width controlling apertures have been removed;

using a CCTV and monitor to view the area to be staked and adjusting the position of the x-y table so that the receiving hole with inserted fixation member end is located in the path that a laser beam emitted from the Nd YAG laser would follow when the laser is energized;

energizing the apertureless Nd YAG laser to produce a multi-mode diffuse laser energy beam of at most about 14 watts;

passing the diffuse laser beam's energy through the optic and to the blue core of the inserted end of the fixation member for about 1.5 seconds;

at least partially melting the sheath of the fixation member so that molten polymethylmethacrylate contacts the cylindrical inner surface of the receiving hole; and staking the inserted end of the fixation member to the lens optic such that, upon cooling, the laser-staked area of the lens is substantially free of heat-induced defects when viewed under a magnification of 10X and the staked fixation element is able to withstand a pull strength of at least 50 g.

2. The method of claim 1 wherein the energizing includes emitting diffused Nd YAG laser energy at about 1064 nm for about 1.5 secs.

3. The method of claim 2 wherein the at least one fixation member comprises a pair of J-shaped or other shaped haptic loops.

* * * * *